United States Patent [19]

Murphy et al.

[11] Patent Number: 4,820,518

[45] Date of Patent: Apr. 11, 1989

[54] COSMETIC POWDER PRODUCT

[75] Inventors: John H. Murphy, Germantown, Tenn.; Ernest S. Curtis, Milford, Pa.; Donald D. Horton, Glen Spey, N.Y.

[73] Assignee: Kolmar Laboratories Inc., Port Jervis, N.Y.

[21] Appl. No.: 940,431

[22] Filed: Dec. 11, 1986

[51] Int. Cl.⁴ .......................... A61K 6/00; B29B 9/00
[52] U.S. Cl. ....................................... 424/401; 424/63; 424/486; 264/7
[58] Field of Search ................ 428/405; 427/219, 221; 424/63, 69, 401, 489, 486, 502; 264/7

[56] References Cited

U.S. PATENT DOCUMENTS

| 2,722,504 | 11/1955 | Fleck | 427/221 X |
| 3,800,034 | 3/1974 | Kircher et al. | 424/63 |
| 3,905,936 | 9/1975 | Hawthorne | 427/221 X |
| 4,337,859 | 7/1982 | Murphy et al. | 206/37 |
| 4,414,200 | 11/1983 | Murphy et al. | 424/63 |
| 4,494,993 | 1/1985 | Bernhard et al. | 106/291 |
| 4,565,581 | 1/1986 | Bernhard | 427/219 |
| 4,656,087 | 4/1987 | Lubianez et al. | 427/219 X |

FOREIGN PATENT DOCUMENTS

| 2122890 | 11/1972 | Fed. Rep. of Germany | 427/221 |
| 2922919 | 12/1979 | Fed. Rep. of Germany | 427/221 |

Primary Examiner—Thurman K. Page
Attorney, Agent, or Firm—Andrus, Sceales, Starke & Sawall

[57] ABSTRACT

A non-pressed cosmetic powder containing hydrophobic inorganic pigments.

13 Claims, No Drawings

COSMETIC POWDER PRODUCT

BACKGROUND OF THE INVENTION

In the past, loose powder cosmetic products were commonly applied to the skin through use of a puff. More recently, pressed powder products, such as face powder, eye shadow, blushes or the like have replaced the loose powder products and are produced by compressing loose powder into a metal pan using direct pressure. The pan containing the pressed powder cake is then glued into a compact or other container.

In the fabrication of pressed powder products, the pressure used in the pressing operation must be maintained within precise limits. If the pressure is too great, the metal pan may be distorted and must be discarded. In addition, utilizing a high pressure results in a cake which lacks the desired payoff characteristics. On the other hand, if the pressure is too low, the pressed cake will lack cohesive strength.

Further, certain powder compositions cannot be successfully used as a pressed powder cake because the pressure required to obtain the necessary cohesive strength will either distort the metal pan or produce a cake that is so hard that it lacks payoff.

To eliminate the problems associated with pressed powder products, non-pressed or poured powder cosmetic products have been proposed, as disclosed in U.S. Pat. Nos. 4,337,859 and 4,414,200. To form a non-pressed cosmetic product, a slurry is initially formed by mixing powdered materials, a binder such as a fatty acid, an evaporable carrier and pigments. The slurry is then poured into a container or mold, and on cooling and evaporation of the carrier, a solid product or cake is produced.

The powder cake, as produced by the aforementioned patents, can be formed directly in the compact or marketing container without the use of a metal pan as is required in pressed powder processes. By eliminating the use of the metal pan, the design configuration of the cake can be increased and the labor and assembly operations are greatly reduced.

It is has been noted that certain inorganic pigments, such as the oxides of iron, chromium and magnesium, possess a high degree of static charge. In a pressed powder product, the static charge does not present problems since the binders used in the pressed powder formulation tend to disperse the charges and the mechanical force of compression tends to hold the cake together.

However, in a non-pressed powder product, as disclosed in the aforementioned patents, the static charge on the pigments can cause color drift during filling and cracking of the cake on drying. These problems are further accentuated when small amounts of water from condensed steam used in the manufacturing process are present in the composition. It has been found that pigments tainted with water are attracted to various parts of the manufacturing equipment, such as the kettle, agitators and filling equipment, with the result that the slurry being poured into the mold or container does not contain all of the pigments of the formulation and shade drift or lack of color can occur when using multiple color pigments.

SUMMARY OF THE INVENTION

The invention is directed to a non-pressed cosmetic powder product containing hydrophobic inorganic pigments which resist color drift and prevent cracking of the cake during drying. The product is formed by mixing cosmetically acceptable powders, a binder, such as a fatty alcohol containing from 12 to 22 carbon atoms, an evaporable carrier and hydrophobic inorganic pigments to form a slurry. The hydrophobic pigments are formed by coating the inorganic pigments with a non-polar, water insoluble, organic coating, such as a polymethylsilicone.

The slurry at an elevated temperature is poured into a mold or container, and on cooling and evaporation of the carrier, a solid powder cake is produced.

The hydrophobic coating on the pigments eliminates static charges and thereby produces a dry powder cake that is homogeneous in composition.

The use of the hydrophobic pigments also eliminates color drift and provides a more predictible color in the final product.

Other objects and advantages will appear in the course of the following description.

DESCRIPTION OF THE PREFERRED EMBODIMENT

The cosmetic powder product of the invention is prepared from a slurry having the following formulation in weight percent:

| | |
|---|---|
| Finely divided inert filler or powder | 70%–10% |
| Binder | 5%–30% |
| Volatile carrier | 25%–60% |
| Cosmetic coloring materials | 1%–15% |

The finally divided filler or powder can take the form of cosmetically acceptable powders such as aluminum hydroxide, kaolin, talc, mica, corn starch, calcium carbonate, silicon dioxide, calcined clay, barium sulfate, aluminum oxide, aluminum silicate, and the like.

The binder is preferably a fatty alcohol that is miscible with the carrier and contains from 12 to 22 carbon atoms in the molecule. The fatty alcohol can preferably take the form of cetyl alcohol, stearyl alcohol, and the like.

The volatile organic carrier is a liquid at room temperature and preferably takes the form of a siloxane composed primarily of two cyclic components: $D_4$ cyclodimethicone and $D_5$ cyclodimethicone. The $D_4$ component represents the majority with the $D_5$ being a minor constitutent. Chemically $D_4$ cyclodimethicone may be symbolically written as:

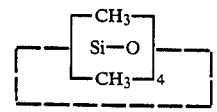

and $D_5$ cyclodimethicone may be symbolically written as:

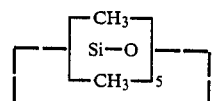

The cosmetically acceptable coloring materials include inorganic pigments such as iron oxide, ultramarines, chromium oxide, chromium hydroxide, titanium dioxide, ferric ferrocyanide, and ferric ammonium ferrocyanide. In addition, the coloring materials can also include organic dyes and lakes and pearlescents.

It has been found that the inorganic pigments normally have a high degree of static charge. In a non-pressed product, as in the invention, the static charge on the inorganic pigments can cause color drift and cracking of the dried cake. In accordance with the invention, these problems are eliminated by coating the inorganic pigments with a non-polar, water insoluble, dielectric material which renders the pigments hydrophobic and eliminates the static charge. The preferred material for coating the inorganic pigments is a polymethylsilicone such as dimethylmethicone. Other coating materials which can be employed are metallic soaps, such as aluminum myristate and aluminum laurate; amino acids such as acylglutamate; oils such as mineral oil; lecithin and the like. The hydrophobic coating is used in an amount of 1% to 3% by weight of the inorganic pigments.

It has been proposed in the past to incorporate antifrictional materials, such as polymethylsilicones, in cosmetic products to provide a smooth feel on application to the skin. However, the polymethylsilicone is used for a different purpose in the composition of the invention in that it provides a hydrophobic coating on the inorganic pigment particles to eliminate the static charge and prevent hydration as well as agglomeration of the particles. In the present composition, the fatty alcohol imports smoothness and slip to the composition.

In addition to the above ingredients, the slurry can also contain small amounts, up to 2% by weight, of fatty acid esters containing from 12 to 22 carbon atoms such as isopropyl myristate or isopropyl palmitate which prevent dusting of the cake, and/or magnesium stearate which aids in preventing glazing of the cake, and/or a preservative such as methyl paraben or propyl paraben, and/or perfumes.

To prepare the cosmetic product of the invention, a liquid slurry is prepared by dispersing the fatty alcohol in the volatile carrier at an elevated temperature, generally in the range of about 60° C. to 70° C. The remaining ingredients, such as the powdered filler, coloring materials and other additives are then mixed into the liquid dispersion to provide the slurry. The slurry, at a temperature of about 50° C. to 60° C., is then poured by gravity into a container or mold, and on cooling to a temperature below about 45° C. the slurry will solidify to form a solid cake.

Subsequently the cake is dried, preferably at an elevated temperature of about 40° C. for about 60 hours to evaporate the carrier from the cake so that the dried cake has a residual carrier content of less than 2% by weight. While it is possible to evaporate all the carrier, it is normally uneconomical to go beyond the 2% level. The resulting cake can then be packaged in a conventional manner.

The following formulations in weight percent illustrate the preparation of poured powder products in accordance with the invention:

| INGREDIENTS | Example No. 1 - BLUSHER |
|---|---|
| Silicone SF 1173 | 38.00 |
| Alumina 617 | 32.71 |
| Stearyl Alcohol | 8.50 |
| Ethyl Hexyl Palmitate | 1.00 |
| Magnesium Stearate | 1.05 |
| Biron HB | 6.30 |
| Methyl Paraben | 0.13 |
| Propyl Paraben | 0.05 |
| Germall 115 | 0.08 |
| Mineral Oil | 0.43 |
| Silicone 1107 | 0.03 |
| Tenox BHA | 0.01 |
| C-19-003 D&C Red #7 | 0.96 |
| Coated 9111 Cosmetic Brown | 1.60 |
| Coated 9124 Red Iron Oxide | 1.39 |
| Coated D9510 Ultramarine Blue | 0.37 |
| Mica M | 5.25 |
| Timica Pearl White | 1.07 |
| MP 1001 Pearl | 1.07 |
| | 100.00% |

| INGREDIENTS | Example No. 2 - BLUSHER |
|---|---|
| Silicone SF 1173 | 38.00 |
| Alumina 617 | 26.92 |
| Stearyl Alcohol | 8.50 |
| Ethyl Hexyl Palmitate | 1.00 |
| Magnesium Stearate | 1.05 |
| Biron HB | 6.30 |
| Methyl Paraben | 0.13 |
| Propyl Paraben | 0.05 |
| Germall 115 | 0.08 |
| Mineral Oil | 0.43 |
| Silicone 1107 | 0.03 |
| Tenox BHA | 0.01 |
| Coated 9124 Red Iron Oxide | 0.65 |
| Mica M | 5.25 |
| MP 101 Pearl | 10.94 |
| 6506 D&C Red #6 | 0.66 |
| | 100.00% |

| INGREDIENTS | Example No. 3 - EYESHADOW |
|---|---|
| Silicone SF 1173 | 38.00 |
| Alumina 617 | 25.70 |
| Stearyl Alcohol | 8.50 |
| Ethyl Hexyl Palmitate | 1.00 |
| Magnesium Stearate | 1.05 |
| Biron HB | 2.63 |
| Methyl Paraben | 0.13 |
| Propyl Paraben | 0.05 |
| Germall 115 | 0.08 |
| Mineral Oil | 1.57 |
| Tenox BHA | 0.01 |
| Coated D9510 Ultramarine Blue | 3.80 |
| Mica M | 5.83 |
| Timica Pearl White | 0.58 |
| Coated D9146 Black Iron Oxide | 2.33 |
| Coated D9210 Maganese Violet | 2.91 |
| Cloissone Blue | 5.83 |
| | 100.00% |

| INGREDIENTS | Example No. 4 - EYESHADOW |
|---|---|
| Silicone SF 1173 | 38.00 |
| Alumina 617 | 21.90 |
| Stearyl Alcohol | 8.50 |
| Ethyl Hexyl Palmitate | 1.00 |
| Magnesium Stearate | 1.05 |
| Biron HB | 6.82 |
| Methyl Paraben | 0.13 |
| Propyl Paraben | 0.05 |
| Germall 115 | 0.08 |
| Mineral Oil | 3.03 |
| Tenox BHA | 0.01 |
| Coated D9510 Ultramarine Blue | 0.87 |
| Mica M | 3.25 |
| Coated D9146 Black Iron Oxide | 0.11 |
| Cloissone Blue | 5.41 |
| Coated D9310 Chromium Hydroxide Green | 0.05 |
| Flamenco Super Pearl 100 | 9.74 |
| | 100.00% |

| INGREDIENTS | Example No. 5 |
|---|---|

| -continued | |
|---|---|
| Silicone SF1173 | 38.00 |
| Alumina 617 | 10.69 |
| Stearyl Alcohol | 8.50 |
| Ethyl Hexyl Palmitate | 1.00 |
| Magnesium Stearate | 1.05 |
| Biron HB | 6.30 |
| Methyl Paraben | 0.13 |
| Propyl Paraben | 0.05 |
| Germall 115 | 0.08 |
| Tenox BHA | 0.01 |
| Silicone Coated Chromium Hydroxide Green | 0.74 |
| Amino Acid Treated Black Iron Oxide | 3.18 |
| Silicone Coated Ultramarine Blue | 0.21 |
| Amino Acid Treated Yellow Iron Oxide | 1.48 |
| Mineral Oil | 3.18 |
| Mica M | 2.63 |
| Cloisonne Green | 12.71 |
| Colorona Dark Blue | 10.06 |
| | 100.00% |

| INGREDIENTS | Example No. 6 |
|---|---|
| Silicone SF1173 | 38.00 |
| Alumina 617 | 21.47 |
| Stearyl Alcohol | 8.50 |
| Ethyl Hexyl Palmitate | 1.00 |
| Magnesium Stearate | 1.05 |
| Biron HB | 5.25 |
| Methyl Paraben | 0.13 |
| Propyl Paraben | 0.05 |
| Germall 115 | 0.08 |
| Tenox BHA | 0.01 |
| Mineral Oil | 3.57 |
| Mica M | 2.63 |
| Silicone Coated Cosmetic Brown | 0.06 |
| Metal Soap Treated Yellow Iron Oxide | 0.30 |
| Silicone 1107 Fluid | 0.03 |
| Flamenco Gold 100 | 17.87 |
| | 100.00% |

In all of the above examples, the fatty alcohol was added to the liquid siloxane at a temperature of 65° C. and the remaining ingredients were then blended into the liquid to form a slurry. In each case the slurry, at a temperature of about 55° C. was poured into plastic molds to form the products. Air at a temperature of 28° C. was passed over the products for a period of 72 hours to evaporate the major proportion of the siloxane to provide the finished product composition. In each example the dried product had a residual siloxane content of less than 2% by weight.

In molding the product, the slurry can be poured directly into a component of the final package, or alternately, the slurry can be introduced into a separate mold or container and subsequently transferred to the package.

The product of the invention can be used to produce a wide variety of cosmetic or pharmaceutical products such as face powders, rouges, blushes, antiperspirants, eye shadows, deodorants, and the like.

Through use of the coated inorganic pigments, the pigments are hydrophobic and free of static charge so that any water associated with steam condensation during the manufacturing process will not cause color drift and a more predictable color can be achieved in the final poured powder product.

By eliminating the static charge on the inorganic pigments, a more uniform product is achieved which will not crack during the drying operation.

Various modes of carrying out the invention are contemplated as being within the scope of the following claims particularly pointing out and distinctly claiming the subject matter which is regarded as the invention.

We claim:

1. A non-pressed solid powder cosmetic product, comprising a mixture of a finely divided cosmetically acceptable filler, an organic binder, an evaporable organic carrier, and cosmetic coloring materials, said cosmetic coloring materials including inorganic pigments coated with a non-polar water insoluble organic dielectric material, said coated pigments being hydrophobic and free of static charge.

2. The product of claim 1, wherein said binder is an organic fatty alcohol containing from 12 to 22 carbon atoms and said carrier is a liquid volatile cyclic siloxane.

3. The product of claim 1, wherein said pigments are selected from the group of iron oxides, magnesium oxides, chromium oxides, and mixtures thereof.

4. A non-pressed solid powder cosmetic product, comprising a mixture of a finely divided cosmetically acceptable filler, an organic binder, an evaporable organic carrier, and cosmetic coloring materials, said cosmetic coloring materials including inorganic pigments coated with a polymethylsilicone.

5. The product of claim 4, wherein said polymethylsilicone is dimethylmethicone.

6. A non-pressed solid powder cosmetic product, comprising a mixture of a finely divided cosmetically acceptable filler, a fatty alcohol containing from 12 to 22 carbon atoms, a residual amount of an evaporable liquid cyclic siloxane, and cosmetic coloring materials including inorganic pigment particles having a static charge and coated with a non-polar water insoluble organic coating material to provide a hydrophobic static-free coating on said particles.

7. The product of claim 6, wherein said coating material comprises from 1% to 3% by weight of said particles.

8. The product of claim 6, wherein said coating material is selected from the group consisting of dimethylsilicones, metallic soaps, amino acids, oils, lecithin, and mixtures thereof.

9. A method of producing a non-pressed cosmetic powder product, comprising the steps of coating inorganic cosmetic pigment particles with an organic non-polar water insoluble coating to provide a hydrophobic substantially static free coating on said particles, mixing the coated pigment particles with a finely divided cosmetically acceptable filler, an organic binder and a liquid evaporable carrier to form a slurry, pouring the slurry into a mold to form a molded product, and evaporating the carrier while maintaining said product under atmospheric pressure to form a dried cosmetic powder product.

10. A method of producing a non-pressed cosmetic powder product, comprising the steps of coating inorganic cosmetic pigment particles with a polymethylsilicone to provide a hydrophobic substantially static free coating on said particles, mixing the coated pigment particles with a finely divided cosmetically acceptable filler, an organic binder and a liquid evaporable carrier to form a slurry, pouring the slurry into a mold to form a molded product, and evaporating the carrier while maintaining said product under atmospheric pressure to form a dried cosmetic powder product.

11. The method of claim 9, wherein said slurry is poured under atmospheric pressure into said mold.

12. The method of claim 9, wherein said inorganic pigments contain a metal selected from the group consisting of iron, magnesium, chromium and mixtures thereof.

13. A method of producing a non-pressed cosmetic powder product, comprising the steps of coating inorganic cosmetic pigment particles with an organic non-polar water insoluble coating to provide a hydrophobic substantially static free coating on said particles, mixing the coated pigment particles with a finely divided cosmetically acceptable filler, an organic binder and a liquid evaporable carrier in the following amounts by weight to form a slurry:

| | |
|---|---|
| Filler | 70%–10% |
| Binder | 5%–30% |
| Carrier | 25%–60% |
| Coated pigment particles | 1%–15% | pouring the slurry into a mold to form a molded product, and evaporating the carrier to reduce the carrier to a residual amount less than 2% by weight of said composition while maintaining said product under atmospheric pressure to form a dried cosmetic powder product.

* * * * *